United States Patent
James

(10) Patent No.: US 10,955,503 B2
(45) Date of Patent: Mar. 23, 2021

(54) METHOD TO MEASURE TISSUE TEXTURE USING NMR SPECTROSCOPY WITH VOI LENGTH IN AN ANALYSIS DIRECTION DEFINED BY RECEIVER BANDWIDTH

(71) Applicant: BIOPROTONICS, INC>, Santa Barbara, CA (US)

(72) Inventor: Timothy W. James, Santa Barbara, CA (US)

(73) Assignee: BIOPROTONICS, inC., Santa Barbara, CA (US)

( * ) Notice: Subject to any disclaimer, the term of this patent is extended or adjusted under 35 U.S.C. 154(b) by 0 days.

(21) Appl. No.: 16/689,761

(22) Filed: Nov. 20, 2019

(65) Prior Publication Data

US 2020/0088825 A1    Mar. 19, 2020

Related U.S. Application Data

(60) Continuation-in-part of application No. 16/450,361, filed on Jun. 24, 2019, which is a continuation of
(Continued)

(51) Int. Cl.
*G01R 33/56* (2006.01)
*G06T 7/00* (2017.01)
(Continued)

(52) U.S. Cl.
CPC .......... *G01R 33/5601* (2013.01); *A61B 5/055* (2013.01); *A61B 5/7203* (2013.01); *G01R 33/4818* (2013.01); *G01R 33/4833* (2013.01); *G01R 33/4835* (2013.01); *G01R 33/5602* (2013.01); *G01R 33/5619* (2013.01); *G01R 33/56341* (2013.01); *G06T 7/0012* (2013.01); *A61B 5/7207* (2013.01);
(Continued)

(58) Field of Classification Search
CPC ............ G01R 33/5601; G01R 33/4818; G01R 33/4833; G01R 33/4235; G01R 33/5602; G01R 33/56341; G01R 33/5619; G06T 7/0012; A61B 5/055; A61B 5/7203
See application file for complete search history.

(56) References Cited

U.S. PATENT DOCUMENTS 9,366,738 B2 *   6/2016   Chase ................ G01R 33/4833
9,664,759 B2 *   5/2017   James .................... A61B 5/055
(Continued)

*Primary Examiner* — Dixomara Vargas
(74) *Attorney, Agent, or Firm* — Felix L. Fischer

(57) ABSTRACT

A method for selective sampling to assess texture of a specimen using magnetic resonance (MR) excites the specimen and refocuses to provide a sample rod within the specimen. An encoding gradient pulse is applied to induce phase wrap creating a spatial encode for a specific k-value and orientation. A low non-zero magnitude gradient is then applied acting as a time dependent phase encode to produce a time varying trajectory through 3D k-space of k-value encodes while simultaneously recording multiple sequential samples of the signal at a sequence of k-values proximate the specific k-value. The receiver bandwidth is set to delineate a length of a VOI within the rod during the data sampling. The samples are then post processed at the sequence of k values, recorded within a time span while the non-zero magnitude gradient is applied, to characterize the textural features of tissue in the VOI.

8 Claims, 3 Drawing Sheets

Related U.S. Application Data application No. 16/044,393, filed on Jul. 24, 2018, now Pat. No. 10,330,763, which is a division of application No. 15/604,465, filed on May 24, 2017, now Pat. No. 10,061,003, which is a continuation-in-part of application No. 15/288,974, filed on Oct. 7, 2016, now Pat. No. 9,664,760, which is a continuation-in-part of application No. 15/167,828, filed on May 27, 2016, now Pat. No. 9,664,759, which is a continuation-in-part of application No. 14/840,327, filed on Aug. 31, 2015, now Pat. No. 9,366,738.

(60) Provisional application No. 62/769,666, filed on Nov. 20, 2018, provisional application No. 62/044,321, filed on Sep. 1, 2014, provisional application No. 62/064,206, filed on Oct. 15, 2014, provisional application No. 62/107,465, filed on Jan. 25, 2015, provisional application No. 62/302,577, filed on Mar. 2, 2016, provisional application No. 62/238,121, filed on Oct. 7, 2015, provisional application No. 62/382,695, filed on Sep. 1, 2016.

(51) Int. Cl.
*A61B 5/055* (2006.01)
*G01R 33/48* (2006.01)
*G01R 33/483* (2006.01)
*G01R 33/563* (2006.01)
*A61B 5/00* (2006.01)
*G01R 33/561* (2006.01)
*G01R 33/50* (2006.01)

(52) U.S. Cl.
CPC ...... *A61B 2560/0238* (2013.01); *G01R 33/50* (2013.01); *G01R 33/5616* (2013.01); *G01R 33/5617* (2013.01); *G06T 2207/10088* (2013.01)

(56) References Cited

U.S. PATENT DOCUMENTS

| | | | |
|---|---|---|---|
| 9,664,760 B2 * | 5/2017 | James | G01R 33/4818 |
| 10,061,003 B2 * | 8/2018 | James | G01R 33/5602 |
| 10,330,763 B2 * | 6/2019 | James | G01R 33/4818 |
| 2016/0061917 A1 * | 3/2016 | Chase | G01R 33/54 324/309 |
| 2016/0274203 A1 * | 9/2016 | James | G01R 33/4818 |
| 2017/0030986 A1 * | 2/2017 | James | G01R 33/5602 |
| 2017/0261584 A1 * | 9/2017 | James | G01R 33/4835 |
| 2018/0329009 A1 * | 11/2018 | James | G01R 33/4818 |
| 2019/0310338 A1 * | 10/2019 | James | A61B 5/7203 |

\* cited by examiner

METHOD TO MEASURE TISSUE TEXTURE USING NMR SPECTROSCOPY WITH VOI LENGTH IN AN ANALYSIS DIRECTION DEFINED BY RECEIVER BANDWIDTH

REFERENCE TO RELATED APPLICATIONS

This application claims priority of U.S. Provisional application Ser. No. 62/769,666 filed on Nov. 20, 2018 entitled A METHOD TO MEASURE TISSUE TEXTURE USING NMR SPECTROSCOPY WITH VOI LENGTH IN AN ANALYSIS DIRECTION DEFINED BY RECEIVER BANDWIDTH, having a common assignee with the present application, the disclosure of which is incorporated herein by reference. This application is a continuation in part of U.S. application Ser. No. 16/450,361 filed on Jun. 24, 2019 which is a continuation of application Ser. No. 16/044,393 filed on Jul. 24, 2018, now U.S. patent Ser. No. 10/330,763, which is a divisional of application Ser. No. 15/604,465 filed on May 24, 2017, now U.S. patent Ser. No. 10/061,003, which is a continuation in part of application Ser. No. 15/288,974 filed on Oct. 7, 2016, now U.S. Pat. No. 9,664,760, which is a continuation in part of Ser. No. 15/167,828 filed on May 27, 2016, now U.S. Pat. No. 9,664,759, which is a continuation in part of application Ser. No. 14/840,327 filed on Aug. 31, 2015, now U.S. Pat. No. 9,366,738. Application Ser. No. 14/840,327 relies on the priority of U.S. provisional application Ser. No. 62/044,321 filed on Sep. 1, 2014 entitled SELECTIVE SAMPLING MAGNETIC RESONANCE-BASED METHOD FOR ASSESSING STRUCTURAL SPATIAL FREQUENCIES, Ser. No. 62/064,206 filed on Oct. 15, 2014 having the same title and Ser. No. 62/107,465 filed on Jan. 25, 2015 entitled MICROTEXTURE CHARACTERIZATION BY MRI. Application Ser. No. 15/167,828 additionally relies on the priority of provisional application Ser. No. 62/302,577 filed on Mar. 2, 2016 entitled METHOD FOR ASSESSING STRUCTURAL SPATIAL FREQUENCIES USING HYBRID SAMPLING WITH LOW OR INCREASED GRADIENT FOR ENHANCEMENT OF VERY LOW NOISE SELECTIVE SAMPLING WITH NO GRADIENT. Application Ser. No. 15/288,974 relies on the priority of U.S. provisional application Ser. No. 62/238,121 filed on Oct. 7, 2015 entitled SELECTIVE SAMPLING MAGNETIC RESONANCE-BASED METHOD FOR ASSESSING STRUCTURAL SPATIAL FREQUENCIES and provisional application Ser. No. 62/382,695 filed on Sep. 1, 2016 entitled SELECTIVE SAMPLING FOR ASSESSING STRUCTURAL SPATIAL FREQUENCIES WITH SPECIFIC CONTRAST MECHANISMS. The referenced applications all have a common assignee with the present application and the disclosures thereof are incorporated herein by reference.

FIELD

The herein claimed method relates to the field of assessment of fine textures in biological systems, and in material and structural evaluation in industry and in engineering research. More specifically, the embodiments disclosed herein provide methods for selective excitation of a first slice within the specimen of interest and a second slice selective refocusing sequence to define a rod followed by application of a gradient along an analysis direction sweeping through a small range of k-values with the receiver bandwidth set narrowly to delineate the length of the volume of interest (VOI).

SUMMARY

The disclosure provides a method for selective sampling to assess texture of a specimen using magnetic resonance (MR). A first RF pulse is transmitted with a first gradient chosen for first slice selection in the specimen. A second RF pulse is transmitted with application of a second gradient chosen for slice selective refocusing in a region defined by an intersection of the first slice and a second slice defining a rod within the specimen. An encoding gradient pulse is applied to induce phase wrap to create a spatial encode for a specific k-value and orientation. A low non-zero magnitude gradient is then applied acting as a time dependent phase encode to produce a time varying trajectory through 3D k-space of k-value encodes while simultaneously recording multiple sequential samples of the NMR RF signal at a sequence of k-values across a neighborhood proximate the specific k-value defined by height and pulse width of the non-zero magnitude gradient and setting receiver bandwidth narrowly enough to delineate a length of a VOI within the rod during the data sampling. The samples are then post processed at the sequence of k values, recorded within a time span while the non-zero magnitude gradient is applied, to characterize the textural features of tissue in the VOI.

DETAILED DESCRIPTION

Figure 1:
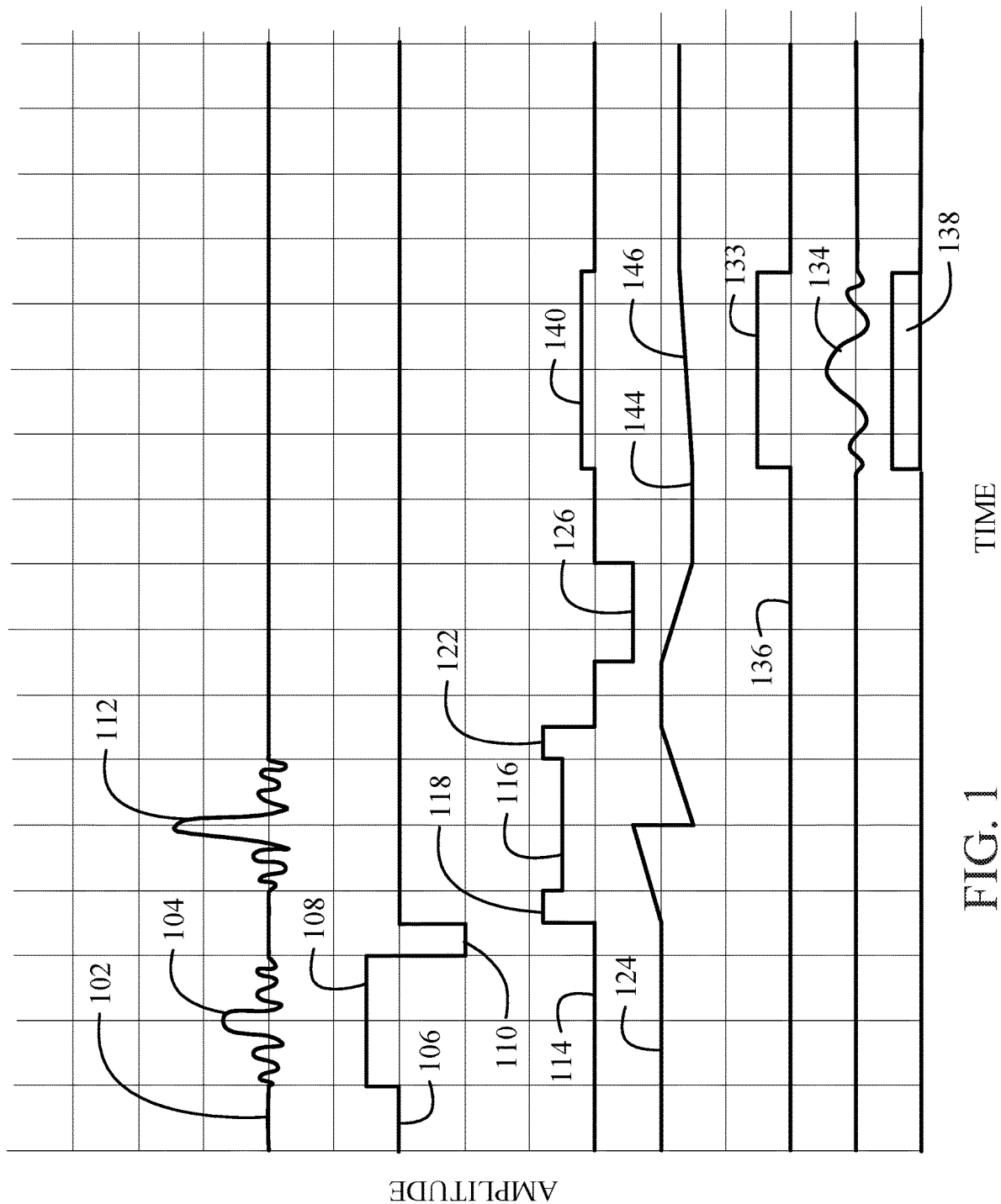
FIG. 1 discloses an example timing diagram of a pulse sequence for the claimed method showing the timing of a single excitation.

Referring to the drawings, FIG. 1 shows an example timing diagram for a pulse sequence for data acquisition using the method claimed herein. RF pulses included in trace 102 are employed to excite selected volumes of the tissue under investigation. A first RF pulse, 104, is transmitted coincidentally with a gradient pulse 108 on a first magnetic field gradient, represented in trace 106. This excites a single slice, or slab, of a specimen, the positioning of which is dependent on the orientation and magnitude of the first gradient, and the frequencies contained in the RF pulse. The negative gradient pulse, pulse 110, rephases the excitation within the defined thickness of the slice or slab.

A second RF pulse 112 is transmitted coincidentally with gradient pulse 116, on a second gradient, represented in trace 114, exciting a slice-selective refocus of spins, this second tissue slice intersecting with the first slice or slab described above. (As this second RF pulse 112 tips the net magnetic vector to antiparallel to Bo, it results in inversion of spins and subsequent refocusing, thus leading to a signal echo at a time after the 180 degree RF pulse equivalent to the time between the 90° and 180° RF pulses.) For the example shown, an initial higher value gradient pulse, 118, at the start of gradient pulse 116 is a crusher, or "spoiler" gradient, designed to induce a large phase wrap across the specimen volume. A similar gradient pulse, 122, at the trailing end of pulse 116, as it comes after the 180 degree RF inversion pulse 112, unwinds this phase wrap. In this way, any excitation that is not present prior to the 180 degree RF pulse, such as excitations from imperfections in the 180 pulse itself, will not have this pre-encode so will not be refocused by the second crusher, hence will not contribute to the signal. Note that the crushers 118 and 122 are shown in FIG. 1 as on only one axis. However, the crushers could be on any combination of axes.

Figure 2:
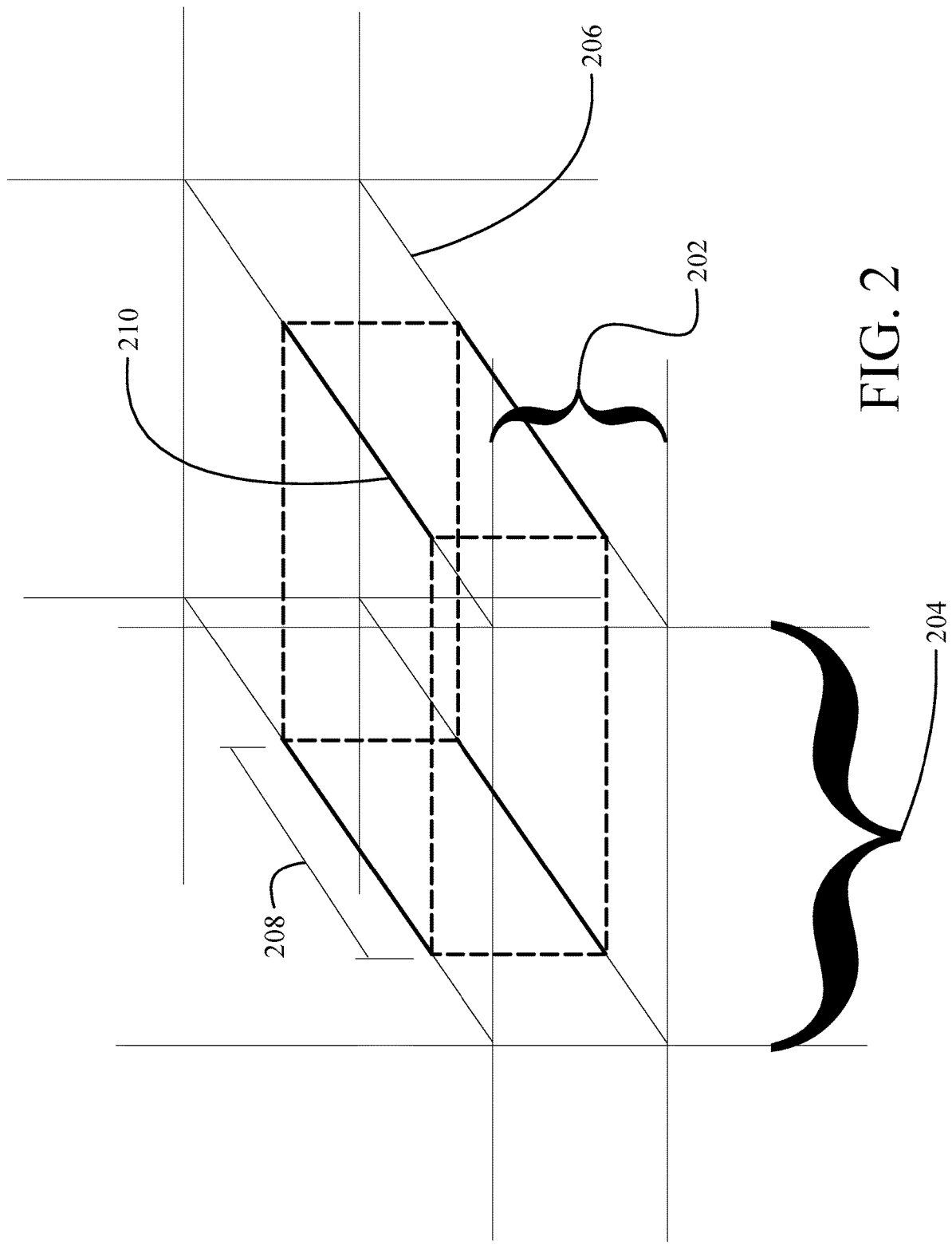
FIG. 2 is a representation of the excited rod or core in the specimen and the resulting selected VOI during data sampling; and, FIG. 3 is a flow chart showing implementation of a method for texture evaluation in the structure of a specimen.

The second RF pulse, in combination with the applied second gradient, provides slice selective refocusing of the signal in a region defined by the intersection of the first slice 202 and the second slice 204 set by this second gradient thereby defining lateral dimensions of a rod or core 206 through the specimen as represented in FIG. 2. Those skilled in the art will recognize that there are a number of ways to generate an internally excited rod using time varying gradient pulses and RF excitations. Parameter selection for the various methods can be done with SNR optimization in mind. As described herein the rod or core 206 generated by a slice selective excitation and mutually-orthogonal slice selective refocusing pulses is represented in FIG. 2.

An encoding gradient pulse 126, on trace 114, sets an initial phase wrap, hence k-value encode, along the direction of gradient pulse 126. In general, the k-value encode can be oriented in any direction, by vector combination of the machine gradients but for ease of visualization is represented as on the second gradient. The negative encoding gradient pulse 126 winds up phase such that, in the signal echo signal acquisition starts at selected k-value, which may then be subsequently incremented or incremented or varied in orientation. While shown separated from second gradient pulse 116, the encoding gradient pulse 126 may be combined with pulse 122.

A low non-zero magnitude phase encode gradient 140 acting as a time dependent phase encode is applied and data samples 142 are taken from an initial k-value 144 for time varying k-values, seen in trace segment 146. The encode 140 for the initial k-value and the subsequent time varying k-values 146 do not need to be aligned with the axis of the excited rod. However, alignment of the phase encode gradient is aligned with the delineated direction of the VOI and, by definition aligned with an analysis direction, as described subsequently.

A receive gate 133 is opened to receive the RF signal, which is shown in FIG. 1 as pulse 134 on signal trace 136. The RF signal in trace 136 is a representation showing only the signal present in the receive gate window without showing the actual details of the RF signal outside the window. Sampling occurs as represented by trace 138 beginning with the initial k-value, 144, seen on trace 124. Note that, at the scale of the drawing, the sampling rate is high enough that the individual triggers of the analog to digital converter (A/D) have merged together in trace 138. The receiver bandwidth is set to delineate a length 208 of a VOI 210 within the rod or core 206 (seen in FIG. 2) during the data sampling. The initial phase wrap may be selected to provide an initial k-value with a magnitude corresponding to a low SNR region. The encoding gradient 126 may be employed to wind up to the lowest or highest k-value in a targeted texture and the non-zero magnitude gradient pulse is imposed in the necessary direction (increasing or decreasing k) to reach the other limit in k-space to define the texture. In an exemplary implementation a 50 ms read time (i.e., gradient on time) would be employed with a wavelength range 0.050 to 0.100 mm, Bzero=1T, H1 nucleus (4.258 MHz/T). A VOI analysis length 5 mm could be obtained with a gradient of 23.5 mT/m and bandwidth of ~500 Hz. In practice the data would be acquired in a first VOI with a first significantly larger bandwidth with later data analysis and selection of multiple subset VOIs by post hoc selection of the bandwidth within the data, as described subsequently.

The echo can be refocused within the same excitation and again read with a phase encode gradient of the same magnitude as phase encode gradient 140 but in opposite direction to sweep back through the same range of k-values allowing implementation of phase cycling and achieving a higher SNR.

Using bandwidth to select the specimen length has the additional advantage that the band pass may be offset one way or another within the first bandwidth to access the sample in slightly different regions in the specimen along the same initially excited rod. As an example, the location of the width dimension 208 can also be set by the center frequency of the bandwidth chosen. This way multiple VOIs along the rod 206 defined by the first and second slice 202, 204 may be selected. This can be done by post processing the received broadband data set.

Figure 3:
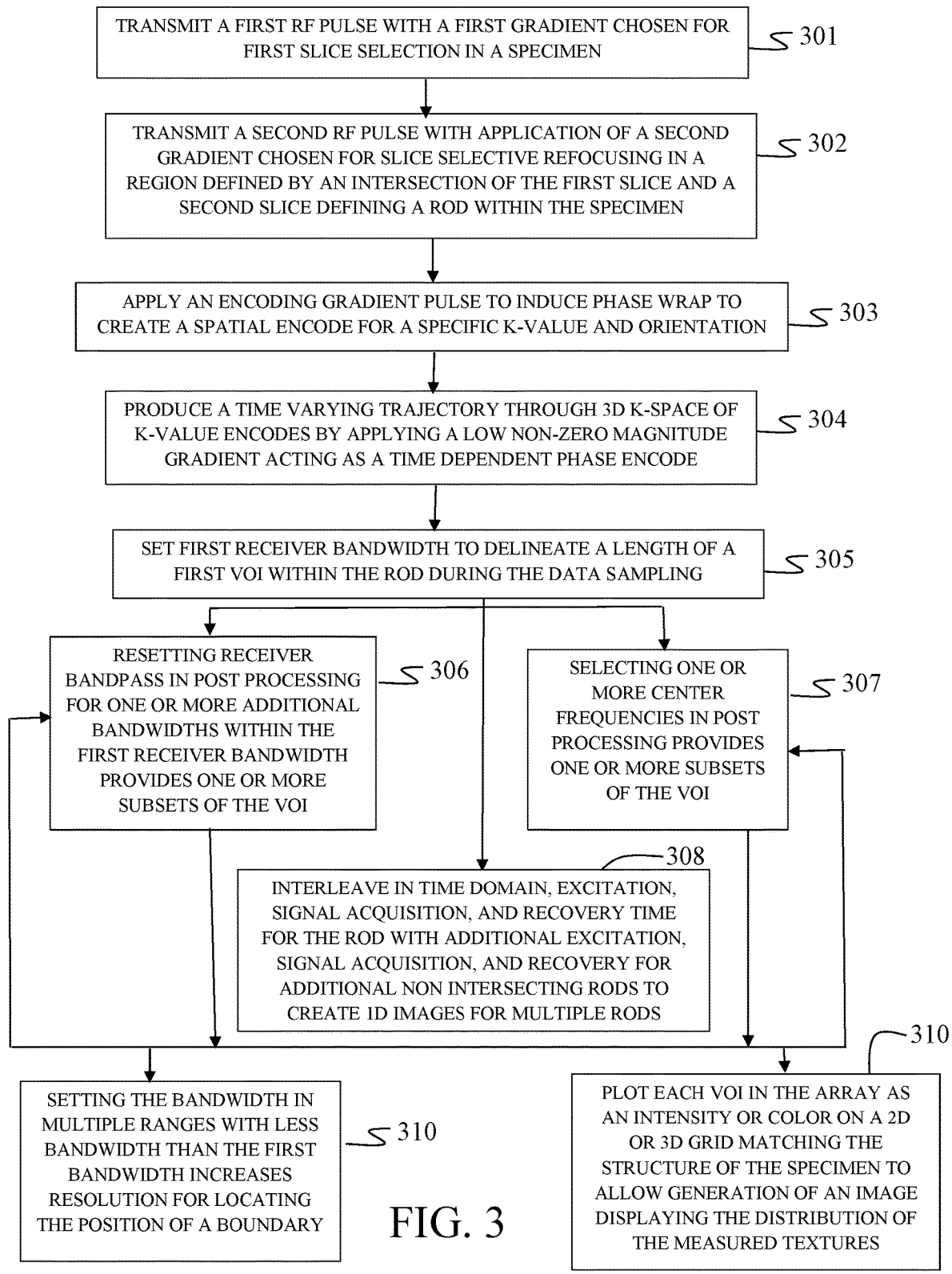

As shown in FIG. 3, an additional aspect of the disclosed method is iterating the disclosed method on an array of VOIs for a plurality of measured or derived values and plotting each VOI in the array as an intensity or color on a 2D or 3D grid matching the structure of the analyzed specimen to generate an image displaying the distribution of the measured textures. The method disclosed here is particularly well suited to efficiently gathering the multiplicity of VOI measurements. For each internally excited rod 206, setting a center frequency and sufficiently large bandwidth to cover the portion of the specimen intended for analysis for a first VOI can then be followed by repetitive selection of varying center frequency and bandwidth for a plurality of subset VOIs and post processing (filtering) along the axis of the gradient (rod 206) and, with each iteration, generating a 1D image of the measured (or derived) values. By interleaving in time domain, the excitation, signal acquisition, and recovery time for a rod with additional excitation, signal acquisition, and recovery for additional non intersecting rods, 1D images for multiple rods can also be efficiently acquired.

This additional aspect provides a sensitive method for locating boundaries of structures in the analyzed specimen for cases where the rod 206 intersects a boundary between differing texture types in the specimen. Setting the bandwidth in multiple narrow ranges within the first bandwidth during post processing has the effect of increasing the resolution for locating the position of the boundary.

Incorporating the excitation pulses and gradients as described with respect to FIG. 1, a first RF pulse is transmitted with a first gradient chosen for first slice selection in a specimen, step 301. A second RF pulse is transmitted with application of a second gradient chosen for slice selective refocusing in a region defined by an intersection of the first slice and a second slice defining a rod within the specimen, step 302. An encoding gradient pulse is applied to induce phase wrap to create a spatial encode for a specific k-value and orientation, step 303. By applying a low non-zero magnitude gradient acting as a time dependent phase encode a time varying trajectory through 3D k-space of k-value encodes is produced, step 304. A first receiver bandwidth is set to delineate a length of a first VOI within the rod during the data sampling, step 305, and multiple sequential samples of the NMR RF signal are simultaneously recorded at a sequence of k-values across a neighborhood proximate the specific k-value defined by height and pulse width of the non-zero magnitude gradient, step 305. The samples of the sequence of k values, recorded within a time span while the non-zero magnitude gradient was applied, are then post processed. Resetting receiver bandpass for one or more additional bandwidths within the first receiver bandwidth provides one or more subsets of the VOI, step 306. Alternatively, or in combination, one or more alternative center frequencies within the first receiver bandwidth are selected to provide one or more subsets of the VOI, step 307. By interleaving in time domain, excitation, signal acquisition, and recovery time for the rod with additional excitation, signal acquisition, and recovery for additional non intersecting rods, 1D images for multiple non-intersecting rods are created, step 308. By iterating for a selected set of pass bands within the first bandwidth to provide an array of VOIs for a plurality of measured or derived values, each VOI in the array may be plotted as an intensity or color on a 2D or 3D grid matching the structure of the specimen to allow generation of an image displaying the distribution of the measured textures, step 309. For identifying boundaries in measured textures in the specimen, setting the bandwidth in multiple ranges with less bandwidth than the first bandwidth increases resolution for locating the position of the boundary, step 310.

Having now described various embodiments of the invention in detail as required by the patent statutes, those skilled in the art will recognize modifications and substitutions to the specific embodiments disclosed herein. Such modifications are within the scope and intent of the present invention as defined in the following claims.

What is claimed is:

1. A method for selective sampling to assess tissue texture using magnetic resonance (MR) comprising:
   transmitting a first RF pulse with a first gradient chosen for first slice selection in a specimen;
   transmitting a second RF pulse with application of a second gradient chosen for slice selective refocusing in a region defined by an intersection of the first slice and a second slice defining a rod within the specimen;
   applying an encoding gradient pulse to induce phase wrap to create a spatial encode for a specific k-value and orientation;
   applying a low non-zero magnitude gradient having a first magnitude acting as a time dependent phase encode to produce a time varying trajectory through 3D k-space of k-value encodes;
   simultaneously recording multiple sequential samples of the NMR RF signal at a sequence of k-values across a neighborhood proximate the specific k-value defined by height and pulse width of the non-zero magnitude gradient in a single excitation;
   setting a first receiver bandwidth to delineate a length of a VOI within the rod during the data sampling; and
   post processing the samples at the sequence of k values, recorded within a time span while the non-zero magnitude gradient is applied, to characterize the textural features of the specimen in the VOI.

2. The method as defined in claim 1 further comprising:
   refocusing;
   applying a low non-zero magnitude gradient with a magnitude equal to but in an opposite direction to the first magnitude;
   simultaneously recording multiple sequential samples of the NMR RF signal in a reverse of the sequence of k-values to sweep back through the same range of k-values allowing implementation of phase cycling.

3. The method as defined in claim 1 further comprising selecting a center frequency of the first receiver bandwidth for positioning of the VOI along the rod.

4. The method as defined in claim 3 wherein the step of post processing includes resetting receiver bandpass for one or more additional bandwidths within the first receiver bandwidth providing one or more subsets of the VOI.

5. The method as defined in claim 3 wherein the step of post processing includes selecting one or more alternative center frequencies within the first receiver bandwidth providing one or more subsets of the VOI.

6. The method as defined in claim 3 further comprising interleaving in time domain, excitation, signal acquisition, and recovery time for the rod with additional excitation, signal acquisition, and recovery for additional non intersecting rods, to create 1D images for multiple rods.

7. A method using magnetic resonance (MR) for generating an image displaying a distribution of measured textures in a specimen comprising:
   transmitting a first RF pulse with a first gradient chosen for first slice selection in a specimen;
   transmitting a second RF pulse with application of a second gradient chosen for slice selective refocusing in a region defined by an intersection of the first slice and a second slice defining a rod within the specimen;
   applying an encoding gradient pulse to induce phase wrap to create a spatial encode for a specific k-value and orientation;
   applying a low non-zero magnitude gradient acting as a time dependent phase encode to produce a time varying trajectory through 3D k-space of k-value encodes;
   setting a first receiver bandwidth to delineate a length of a first VOI within the rod during the data sampling;
   simultaneously recording multiple sequential samples of the NMR RF signal at a sequence of k-values across a neighborhood proximate the specific k-value defined by height and pulse width of the non-zero magnitude gradient;
   post processing the samples at the sequence of k values, recorded within a time span while the non-zero magnitude gradient was applied, iterating a pass band within the first bandwidth providing an array of VOIs for a plurality of measured or derived values; and
   plotting each VOI in the array as an intensity or color on a 2D or 3D grid matching the structure of the specimen to generate an image displaying the distribution of the measured textures.

8. A method using magnetic resonance (MR) for identifying boundaries in measured textures in a specimen comprising:
   transmitting a first RF pulse with a first gradient chosen for first slice selection in a specimen;
   transmitting a second RF pulse with application of a second gradient chosen for slice selective refocusing in a region defined by an intersection of the first slice and a second slice defining a rod within the specimen;
   applying an encoding gradient pulse to induce phase wrap to create a spatial encode for a specific k-value and orientation;
   applying a low non-zero magnitude gradient acting as a time dependent phase encode to produce a time varying trajectory through 3D k-space of k-value encodes;
   setting a first receiver bandwidth to delineate a length of a first VOI within the rod containing a boundary during the data sampling;
   simultaneously recording multiple sequential samples of the NMR RF signal at a sequence of k-values across a neighborhood proximate the specific k-value defined by height and pulse width of the non-zero magnitude gradient; and
   post processing the samples at the sequence of k values, recorded within a time span while the non-zero magnitude gradient was applied, setting the bandwidth in multiple ranges with less bandwidth than the first bandwidth thereby increasing resolution for locating the position of the boundary.

* * * * *